United States Patent [19]

Steiner et al.

[11] Patent Number: 5,046,810
[45] Date of Patent: Sep. 10, 1991

[54] LASER LIGHT APPLICATOR

[75] Inventors: Rudolf Steiner, Ulm/Söflingen; Liu Xiao-Meng, Ulm, both of Fed. Rep. of Germany

[73] Assignee: Richard Wolf GmbH, Knittlingen, Fed. Rep. of Germany

[21] Appl. No.: 542,472

[22] Filed: Jun. 22, 1990

[30] Foreign Application Priority Data

Jul. 25, 1989 [DE] Fed. Rep. of Germany ....... 3924491

[51] Int. Cl.$^5$ .............................................. G02B 6/32
[52] U.S. Cl. ......................................... 385/38; 385/33
[58] Field of Search ........................... 350/96.18, 96.15

[56] References Cited

U.S. PATENT DOCUMENTS

| 4,398,790 | 8/1983 | Righini et al. | 350/96.18 |
| 4,521,070 | 6/1985 | Sottini et al. | 350/96.15 |
| 4,671,609 | 6/1987 | Khoe et al. | 350/96.18 |
| 4,678,268 | 7/1987 | Russo et al. | 350/96.18 |

FOREIGN PATENT DOCUMENTS 0125897 5/1984 European Pat. Off. .

Primary Examiner—Leon Scott, Jr.
Attorney, Agent, or Firm—Panitech, Schwarze, Jacobs & Nadel

[57] ABSTRACT

A laser light applicator comprises a laser light conductor fiber and a light guiding element of larger diameter than the fiber, distally connected thereto by means of a butt joint. The light conductor element is provided at its distal end with a ball head which has been formed with plane, blackened, ground surfaces converging to provide a wedge having at its top a truncated unblackened edge. The ball-head diameter is preferably between 1.5 and 2.0 mm, the plane surfaces being angled by between 54° and 60° with respect to each other.

4 Claims, 1 Drawing Sheet

LASER LIGHT APPLICATOR

FIELD OF THE INVENTION

This invention relates to a laser light applicator for use as a cutter.

BACKGROUND OF THE INVENTION

There is described in EP-B-0 125 897, a laser light applicator comprising a laser light conductor fiber distally connected by welding to a light conductor element of larger diameter than the fiber and which terminates in a wedge shaped tapered portion for use as a cutter.

Although the tapered portion provides a satisfactory guide during the volatilizing of a fabric, said portion terminates in a sharp edge which is subject to intense heating by radiation energy within the tapered portion and is thereby destroyed.

SUMMARY OF THE INVENTION

It is an object of the invention to enable the development of a high degree of heat, during operation of the laser light applicator, under the application of comparatively little power, whilst avoiding destruction of the edge of the tapered portion.

To this end, according light to the invention the conductor element terminates in a ball-like head which has been formed into a wedge defined by two plane, blackened ground surfaces converging to define an unblackened, truncated edge at the tip of the wedge.

The blackening of said plane converging surfaces engenders a high degree of absorption of laser light which does not cause excessive heating of said truncated edge.

The converging plane, blackened, ground surfaces preferably subtend at an angle of 54° to 60° especially where the said head has a diameter of between 1.5 and 2.0 mm. Where the diameter of the ball-like head is larger, blackened wedge surfaces are insufficiently heated and where the said angle is greater, radiation may be reflected back by these blackened surfaces, strike sheathing of the laser fiber and so overheat and destroy it. If, however, the said angle is smaller the radiation may be reflected onto the truncated edge so that it becomes overheated and is thereby destroyed.

DETAILED DESCRIPTION OF THE INVENTION

Figure 1:
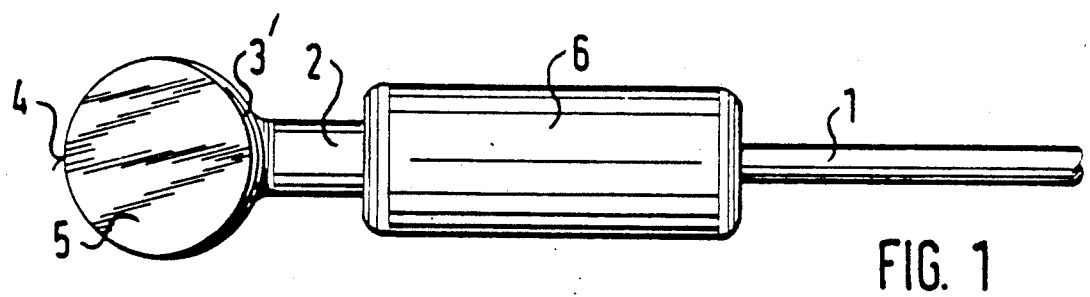
FIG. 1 is a side view of the distal end portion of a laser light applicator, according to an embodiment of the present invention.

Reference will now be made to FIG. 1. A light conductor fiber 1 is butt welded or fused at its distal end to a cylindrical light conductor 2 of larger diameter than the fiber 1. The conductor 2 merges with a head 3 having a diameter of between 1.5 and 2.0 mm and which has been formed with two tapered, plane, ground surfaces 5 which converge to provide a wedge having an unblackened blunt or truncated edge 4 at its tip, the surfaces 5 defining an angle of 54° to 60° therebetween and having been blackened. The transition area between the fiber 1 and the light conductor 2 is surrounded by a cylindrical stabilizing sleeve 6.

Figure 2:
FIGS. 2 to 4 illustrate respective stages in the production of said applicator.
Figure 3:
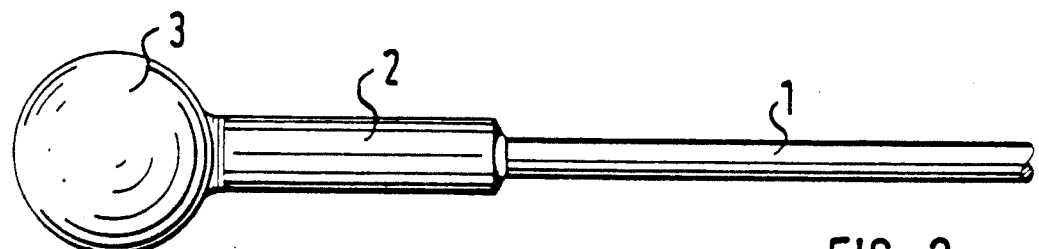
Figure 4:
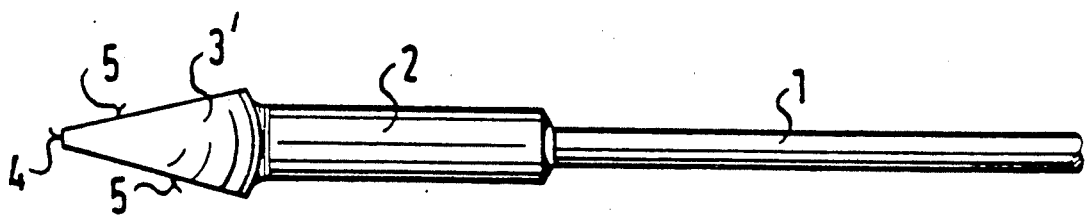

The production of the laser light applicator will now be described with reference to FIGS. 2 to 4. After the fiber 1 has been connected to the conductor 2 (FIG. 2). The conductor 2 is formed with a ball-shaped head 3 as shown in FIG. 3, by heating the conductor 2. The head 3' is then formed with the convergent, plane ground surfaces 5 providing a wedge and defining the blunt or truncated edge 4 at the tip of the wedge (FIG. 4). The stabilizing sleeve 6 is then installed over said transition area. The surfaces 5 are blackened but the edge 4 is not blackened. As will be apparent from FIG. 1, the edge 4 merges arcuately into the remanent ball surface of the head 3'.

What is claimed is:

1. A laser light applicator comprising a laser light conductor fiber (1) and a light conductor element (2) of greater diameter than said fiber (1), said conductor element being connected to the distal end of said fiber and terminating in a circular, wedge-shaped head (3') defined by two planar, blackened surfaces (5) converging to a truncated, unblackened edge (4) at its tip, said planar, blackened surfaces functioning as an absorbent for laser light to serve as a heated cutter, and said planar, blackened surfaces converging at an angle which avoids excessive heating of the truncated, unblackened edge.

2. An applicator according to claim 1, wherein said circular head (3), prior to formation of the wedge shape, had a diameter of between 1.5 mm to 2 mm and said two planar surfaces of said wedge-shaped head (3') define an angle of 54° to 60° between them.

3. An applicator according to claim 1, wherein said truncated edge merges arcuately into remanent curved surfaces of said circular, wedge-shaped head (3').

4. An applicator according to claim 1, wherein said truncated edge merges arcuately into remanent curved surfaces of said circular, wedge-shaped head (3').

* * * * *